United States Patent [19]

Bell

[11] Patent Number: 4,840,625
[45] Date of Patent: Jun. 20, 1989

[54] EXTERNAL CATHETER URINE COLLECTION SYSTEM

[76] Inventor: Ramona R. Bell, 3708 Magee Ave., Oakland, Calif. 94619

[21] Appl. No.: 199,622

[22] Filed: May 27, 1988

[51] Int. Cl.⁴ .............................................. A61F 5/44
[52] U.S. Cl. ..................................... 604/352; 604/349
[58] Field of Search ............... 604/317, 327, 346, 347, 604/348, 349, 350, 351, 352, 353, 355

[56] References Cited

U.S. PATENT DOCUMENTS

| | | | |
|---|---|---|---|
| 2,305,453 | 12/1942 | Martos | 604/346 |
| 2,548,149 | 4/1951 | Fowler, Jr. | 604/347 |
| 3,401,697 | 9/1968 | Lefley et al. | 604/347 |
| 3,739,783 | 6/1973 | Broerman | 604/349 |
| 3,788,324 | 1/1974 | Lim | 604/352 |
| 4,445,898 | 5/1984 | Jensen | 604/337 |
| 4,475,910 | 10/1984 | Conway et al. | 604/349 |
| 4,534,768 | 8/1985 | Osburn et al. | 604/350 |
| 4,588,397 | 5/1986 | Giacalone | 604/349 |
| 4,589,874 | 5/1986 | Riedel et al. | 604/349 |

FOREIGN PATENT DOCUMENTS 2185402 7/1987 United Kingdom ................ 604/346

Primary Examiner—C. Fred Rosenbaum
Assistant Examiner—Mario Costantino
Attorney, Agent, or Firm—Owen, Wickersham & Erickson

[57] ABSTRACT

An external catheter urine collection system includes an external catheter, a urine collection reservoir, and a urine collection tube. The external catheter includes a generally phallic-shaped catheter or condom sheath having a distal and a proximal end. The proximal end of the external catheter is adapted to fit over a male patient's penis and to be positioned at the base of the penis. The distal end of the catheter sheath includes a connector for connecting to the urine collection tube to direct urine from the catheter to the collection tube. A sealing rim is attached to the proximal end of the catheter sheath and is adapted to seal the proximal end of the catheter to the skin adjacent to the base of the patient's penis, thereby securing the catheter to the patient and preventing the leakage of urine from around the proximal end of the catheter sheath.

2 Claims, 1 Drawing Sheet

U.S. Patent    Jun. 20, 1989    4,840,625
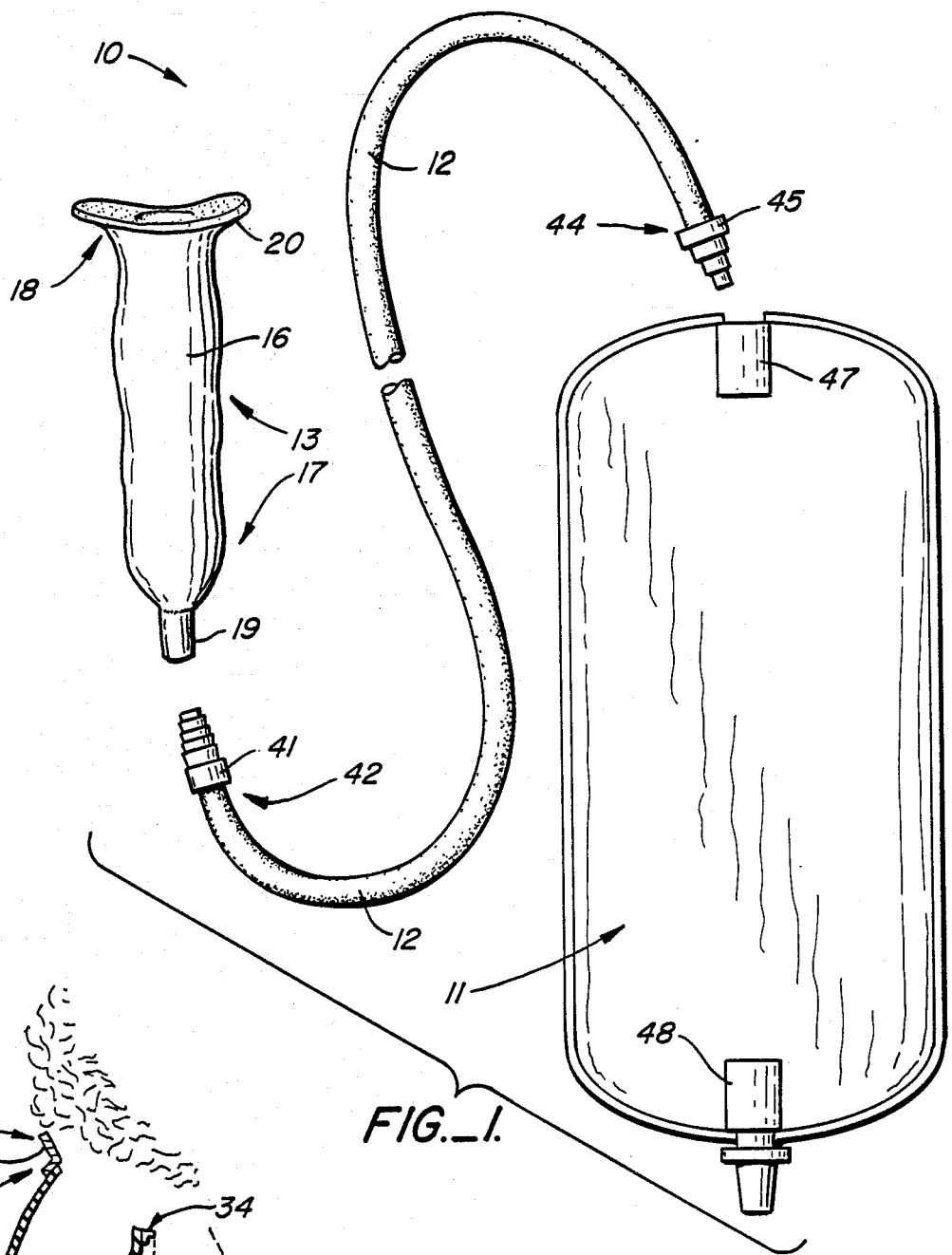
FIG._1.
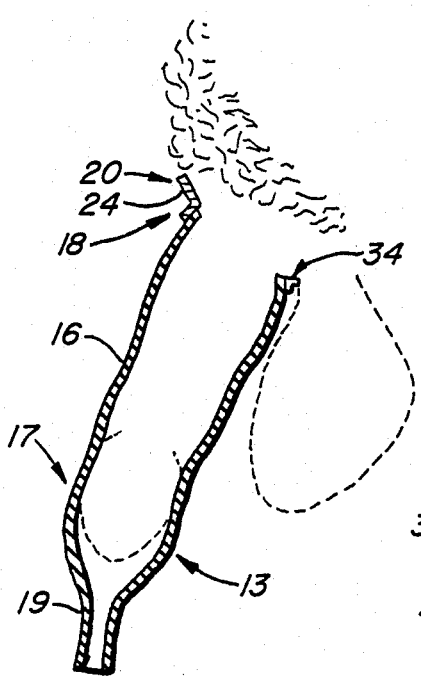
FIG._4.
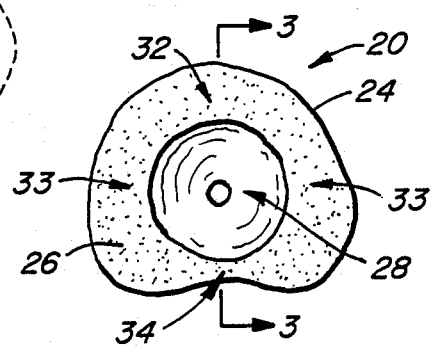
FIG._2.
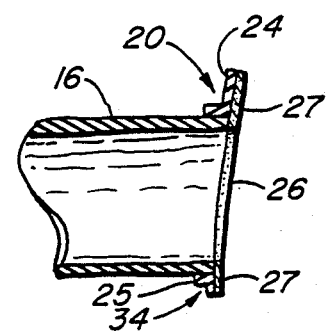
FIG._3.

EXTERNAL CATHETER URINE COLLECTION SYSTEM

The invention relates to urine drainage systems for males an particularly to an improved external catheter urine collection system.

BACKGROUND OF THE INVENTION

The inability of a person to control the flow of urine results from a number of different medical conditions, particularly conditions associated with advanced age. Also, in certain cases a patient for medical treatment may not necessarily be incontinent but may be immobile or may otherwise be unable to relieve himself normally. In these situations it is desirable to provide some means of urine collection.

A number of external catheter systems have been devised for urine drainage for incontinent males. U.S. Pat. No. 4,589,874 to Riedel et al. shows an external catheter in combination with an applicator collar. The catheter includes a thin sheath with an adhesive applied to at least a portion of its inside wall. The sheath is adapted to fit snugly over the patient's penis so that the adhesive coating attaches it directly to the skin of the penile shaft.

A sealant pad for an external catheter is shown in U.S. Pat. No. 4,534,768 to Osburn et al. The sealant pad disclosed by Osburn et al. forms an annular band with an adhesive coating on both its inner and outer surfaces. This sealant pad or band is attached, via the adhesive on its inner surface, to the patients' penis just behind the glans. An external catheter sheath is placed over this pad or band, the outer surface of the band adhering to the catheter sheath so that the band provides a seal between the penis skin and the catheter sheath inside wall. As in the Riedel et al. patent, the catheter sheath shown by Osburn et al. attaches directly to the skin of the penile shaft.

U.S. Pat. No. 4,588,397 to Giacalone also shows an external catheter for males. The Giacalone system includes a pair of specially adapted briefs with an external catheter mounting and sealing collar. The briefs are won by the patent so that the patient's penis extends through an opening in the collar. The catheter sheath fits loosely around the patient's penis and attaches at its proximal end to the collar, which includes a sealing arrangement that contacts the skin toward the base of the penile shaft to form a seal. Although the catheter sheath in the Giacalone system does not contact the penis directly to form a seal, the collar to which the catheter sheath is attached includes a sealing member that contacts the penile shaft to form a seal.

There were a number of problems associated with the prior external catheter systems. In system where the catheter was attached to the skin of the penile shaft, either directly by an adhesive coating as shown by Riedel et al., or indirectly through an adhesive band as shown by Osburn et al., the fit between the penis and the catheter sheath material had to be tight at all times in order to prevent leakage. Furthermore, the fit had to be tight to prevent the catheter sheath from coming off during large flows of urine.

However, if the fit between the penis and the catheter sheath was too tight, the sheath often caused pain or discomfort to the patient generally, and also caused edema, inflammation, and chafing. The problem was exacerbated during involuntary erections. Furthermore, adhesive coated external catheter sheaths were difficult to apply.

Problems also arose with the external catheter system shown by Giacolone. The Giacolone system also obtained a seal against the penile shaft, not with the catheter sheath itself, but with a collar to which the catheter sheath was attached. The collar had to fit tightly to prevent leakage, but if it was too tight, it caused discomfort generally and particularly during involuntary erections. Furthermore, the briefs had to be positioned carefully on the patient and therefore restricted the patient's movement. The briefs were also expensive to produce and greatly increased the cost of the system.

None of the prior external catheters provided a secure, yet comfortable seal and manner of attachment.

It is, therefore, an object of the invention to provide for male patients an external catheter urine collection system that is comfortable to the patient and provides an effective seal to prevent leakage.

Another object of the invention is to provide an external catheter that provides a seal that does not contact the patient's glans or penile shaft.

Another object of the invention is to provide an external catheter that does not restrict the patient's movement.

A further object of the invention is to provide an external catheter that is lightweight and inexpensive to manufacture.

SUMMARY OF THE INVENTION

The present invention marks a departure from prior external catheters that seal against the skin of the patient's penile shaft. Rather, the external catheter of the present invention provides a unique seal with the body skin adjacent to and around the base of the patient's penis. The system includes a urine collection bag or reservoir, a urine collection tube providing a conduit from the catheter to the collection reservoir, and an external catheter with a sealing rim at its proximal end.

In use the external catheter fits loosely over the patient's penis with the proximal end of the catheter secured to and sealed against only the body skin adjacent to and around the base of the penis to prevent leakage. The collection tube acts as a conduit though which urine flows from the external catheter to the collection reservoir, which is positioned conveniently near the patient.

The external catheter includes a generally phallic shaped sheath or condom with an outlet at its distal end. The proximal end of the catheter has a sealing rim attached thereto, the sealing rim having an adhesive surface adapted to contact and seal against the skin adjacent the base of a patient's penis.

The sealing rim comprises a generally asymmetric annular sheet of material with a flange portion by which the rim is attached to the proximal end of the catheter sheath or condom. The annular sheet portion lies substantially in a plane generally perpendicular to the axis of the condom and has a layer of adhesive on its proximal surface in position to adhere only to the body skin adjacent to and around the base of the patient's penis. Also, the annular sheet portion has a unique asymmetrical shape around the circumference of the condom with extended upper and lateral rim areas, and a shorter lower rim area. The upper and lateral rims extend far enough away from the condom to provide a good adhesive contact area to provide a seal and also to secure the catheter to the patient. However, the lower rim extends only a short distance, sufficiently far to provide a seal, but not so far as to rest against the patient's scrotum.

The collection tube and collection bag are both made from lightweight materials, so that their weight does not pull the catheter off. The tube includes at one end a connector adaptor to connect to the outlet at the distal end of the catheter, and at the other end a connector adapted to connect to an inlet connector of the collection bag. The collection bag or reservoir preferably has a capacity of around 1000 to 1200 ml and preferably includes a drain outlet in addition to the inlet connector.

These and other objects, advantages and features of the invention will be apparent from the following description of preferred embodiment, considered along with the accompanying drawings.

BRIEF DESCRIPTION OF THE DRAWINGS

FIG. 1 is a view in elevation of an external catheter system embodying the principles of the present invention.

FIG. 2 is an end view in elevation of the proximal end of the catheter according to the invention.

FIG. 3 is a longitudinal section view of the proximal end of the catheter of FIGS. 1 and 2.

FIG. 4 is a view in section and in elevation of the catheter according to the invention in position on a patient.

DESCRIPTION OF THE PREFERRED EMBODIMENTS

With reference to the figures, FIG. 1 illustrates the overall layout of an external catheter urine collection system 10 according to the present invention. The system 10 includes a specially adapted collection reservoir 11 and a collection tube 12. An external catheter 13 is adapted to be worn over a patient's penis in position to direct urine into the collection reservoir 11 through the collection tube 12.

The external catheter 13 includes a generally phallic-shaped thin flexible catheter sheath or condom 16 having a distal end 17 and a proximal end 18. An outlet connector 19 is located at the distal end 17, and a sealing rim 20 is located at the proximal end 18 of the condom 16. The condom 16 is preferably made from anon-allergenic material such as natural latex rubber, for example.

As shown in FIGS. 2 and 3, the sealing rim 20 comprises a generally asymmetrical annular sheet portion 24 with a flange portion 25 at its inner circumference, the flange portion 25 being sealed to the proximal end 18 of the condom 16. As illustrated in FIG. 2 the annular sheet portion 24 is asymmetrical about the bore 28 of the condom 16. The annular portion 24 includes an upper rim area 32, lateral rim areas 33, and a lower rim area 34. As shown best in FIG. 3, the annular portion 24 has an adhesive layer 27 that covers substantially its entire proximal side 26. Also, in the preferred form the proximal side 26 has a slight concave curvature away from the condom 16.

The sealing rim 20 is preferably on the order of 3mm thick and made in one piece of a soft, spongy, micropore material such as that used as the adhesive base in MEDITRACE electrodes manufactured by Graphic Controls Corporation. The adhesive used for the adhesive layer 27 on the annular portion 24 of the sealing rim 20, is a nonallergenic adhesive, preferably the adhesive used in MEDITRACE electrodes for attaching the electrode to a patient. This combination of sealing rim material and adhesive provides a strong and secure seal only against the patient's body skin adjacent to and around the base of the penis and is minimally affected by moisture.

The illustrated preferred form of the sealing rim 20 includes the flange portion 25 for sealing to the proximal end of the catheter sheath 16. However, the sheet portion 24 of the sealing rim 20 may be attached and sealed to the proximal end of the catheter sheath with any suitable sealing arrangement, and the flange portion 25 may not be required.

In a preferred form illustrated in FIG. 1, the outlet connector 19 at the distal end 17 of the condom 16 comprises a tube of flexible material, and is preferably integrally formed with the condom. This form of connector is lightweight, is easy to manufacture, and connects easily and securely to a connector 41 at a condom-connecting end 42 of the collection tube 12. The connector member 41, in the illustrated form of the invention, is adapted to fit tightly into the flexible tube that forms the outlet connector 19 of the external catheter 13 to form a secure seal. Although the illustrated outlet connector and collection tube connector are preferred forms, any suitable lightweight connecting means can be used to connect the external catheter 13 to the collection tube 12.

The preferred collection tube 12 also includes a reservoir end 44 with a reservoir end connector 45 for connecting the tube 12 to the collection reservoir 11. The connector 45 is preferably a male end connector, similar to the connector 41, and is adapted to fit snugly into a reservoir inlet connector 47 positioned at one end of the reservoir 11. The reservoir also preferably includes a fluid drain 48 for draining reservoir 11 without removing the reservoir from the tube 12 and external catheter 13.

The collection tube 12 and collection reservoir 11 are both made of a suitable lightweight, pliable plastic material such as MEDICAL VINYL used in cath try A by Kendall Company of Boston, Mass.

FIG. 4 shows the external catheter 13 in position on a patient. The catheter sheath or condom 16 fits over the patient's penis with the sealing rim 20 at the condom's proximal end 18 forming an adhesive seal against the skin adjacent the base of the patient's penis. The unique asymmetrical annular shape of the annular sheet portion 24 of the sealing rim 20 provides a large enough adhesive coated surface to provide a secure seal, yet the lower rim area 34 is short enough so as not to rest on the patient's scrotum.

The above described preferred embodiments are intended to illustrate the principles of the invention, but not to limit the scope of the invention. Various other embodiments and modifications to these preferred embodiments may be made by those skilled in the art, without departing from the scope of the following claims.

What is claimed is:

1. An external catheter urine collection system for males, comprising:
   a lightweight urine collection reservoir made of flexible material and having a urine collection inlet,
   a lightweight urine collection tube made of flexible material, having a reservoir connecting end for connecting to the inlet of the urine collection reservoir, and a catheter connecting end means, and
   an external catheter having a distal end and a proximal end, the proximal end having a diameter and length sufficient to fit over a male patient's penis and be positioned at the base of the penis, the distal end including connector means for connecting the catheter to the catheter connecting end of the urine collection tube, so that urine may flow from the catheter into the urine collection tube, and the proximal end including adhesively sealing rim means for sealing the proximal end of the catheter only to the body skin adjacent to and around the base of the patient's penis, thereby adhesively securing the catheter to the patient and preventing leakage of urine from around the proximal end of the catheter, the external catheter including a generally annular sheet of material sealed to and extending around the proximal end of the external catheter, said sheet having an adhesive coated proximal side in position to contact and sealingly adhere to the patient's skin adjacent to the base of the penis, the annular sheet being radially asymmetrical around the proximal end of the external catheter so that when the catheter is properly attached to the patient, no portion of the annular sheet rest substantially on the patient's scrotum.

2. An external catheter for males, for use in a urine collection system in which urine is drained from a patient through a urine collection tube, said external catheter comprising:

a generally phallic shaped condom sheath made of a flexible material and having a distal end and a proximal end, the proximal end having a diameter and length sufficient to fit over a male patient's penis and be positioned at the base of the penis, outlet connector means located at the distal end of the condom for connecting to the urine collection tube of the urine collection system so as to allow urine to flow from the condom into the collection tube, and adhesively sealing rim means located at the proximal end of the condom for adhesively sealing the proximal end of the condom only to the body skin adjacent to and around the base of the patient's penis, thereby securing the condom to the patient and preventing leakage of urine from around the proximal end of the condom, said sealing rim means including a generally annular sheet of material sealed to and extending around the proximal end of the condom, said sheet having an adhesive coated proximal side in position to contact and sealingly adhere to the patient's skin adjacent to the base of the penis, the annular sheet being radially asymmetrical around the proximal end of the condom so that when the catheter is properly attached to the patient, no portion of the sheet rests substantially on the patient's scrotum.

* * * * *

UNITED STATES PATENT AND TRADEMARK OFFICE
CERTIFICATE OF CORRECTION

PATENT NO. : 4,840,625
DATED : June 20, 1989
INVENTOR(S) : RAMONA R. BELL

It is certified that error appears in the above-identified patent and that said Letters Patent is hereby corrected as shown below:

Column 1, line 6: "an" (first occurrence) should read --and--

Column 1, line 44: "won" should read --worn--

Column 1, line 44: "patent" should read --patient--

Column 1, line 55: "system" should read --systems--

Column 4, line 38: "try" should read --tray--

Column 5, line 24: "rest" should read --rests--

Signed and Sealed this

Nineteenth Day of June, 1990

Attest:

HARRY F. MANBECK, JR.

*Attesting Officer*  *Commissioner of Patents and Trademarks*